United States Patent [19]

Albert

[11] Patent Number: 5,237,598

[45] Date of Patent: Aug. 17, 1993

[54] MULTIPLE IMAGE SCANNING X-RAY METHOD AND APPARATUS

[76] Inventor: Richard D. Albert, 317 Hartford Rd., Danville, Calif. 94526

[21] Appl. No.: 872,984

[22] Filed: Apr. 24, 1992

[51] Int. Cl.⁵ ........................................... G01N 23/04
[52] U.S. Cl. ........................................ 378/99; 378/62; 378/57; 378/146; 378/198
[58] Field of Search ................... 378/99, 62, 58, 193, 378/197, 196, 189, 198, 57, 55, 146

[56] References Cited

U.S. PATENT DOCUMENTS

| | | | |
|---|---|---|---|
| 3,949,229 | 4/1976 | Albert | 250/401 |
| 4,144,457 | 3/1979 | Albert | 250/445 |
| 4,149,076 | 4/1979 | Albert | 250/402 |
| 4,196,351 | 4/1980 | Albert | 250/416 |
| 4,288,697 | 9/1981 | Albert | 250/502 |
| 4,730,350 | 3/1988 | Albert | 378/10 |
| 4,737,972 | 4/1988 | Schoolman | 378/99 |
| 4,907,157 | 3/1990 | Uyama et al. | 378/196 |

*Primary Examiner*—David P. Porta
*Assistant Examiner*—Don Wong
*Attorney, Agent, or Firm*—Harris Zimmerman

[57] ABSTRACT

X-ray examination of objects, which may be very large objects such as aircraft, boat hulls or lengthy pipelines, is accomplished with an x-ray source having a moving x-ray origin point that is scanned in a raster pattern. At least one x-ray detector having a very small x-ray sensitive area is disposed behind or within the object and provides an output signal indicative of internal characteristics of an adjacent region of the object. The source and detector undergo relative travel at least in a lateral direction during the examination to provide a sequence of different x-ray views that may include views of successive regions of the object, views from different angles and stereo views. X-ray images are produced at one or more monitor screens by sweeping a point of light in a raster pattern corresponding to that of the x-ray source while modulating the intensity of the point of light in accordance with the output signal of the detector. An array of spaced apart detectors may be used to simplify examination of large objects or to speed examination of small objects.

31 Claims, 8 Drawing Sheets

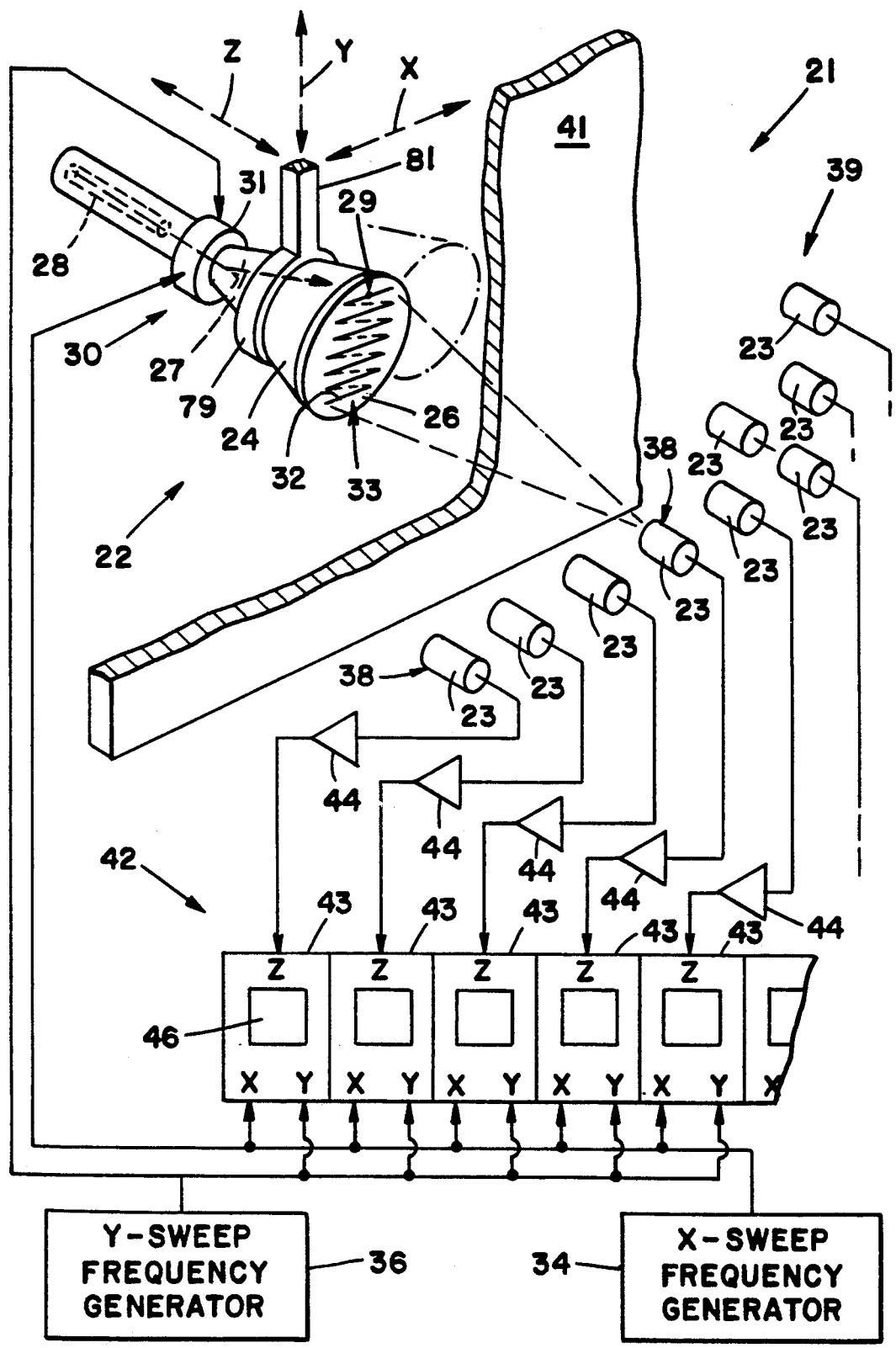
FIG_1

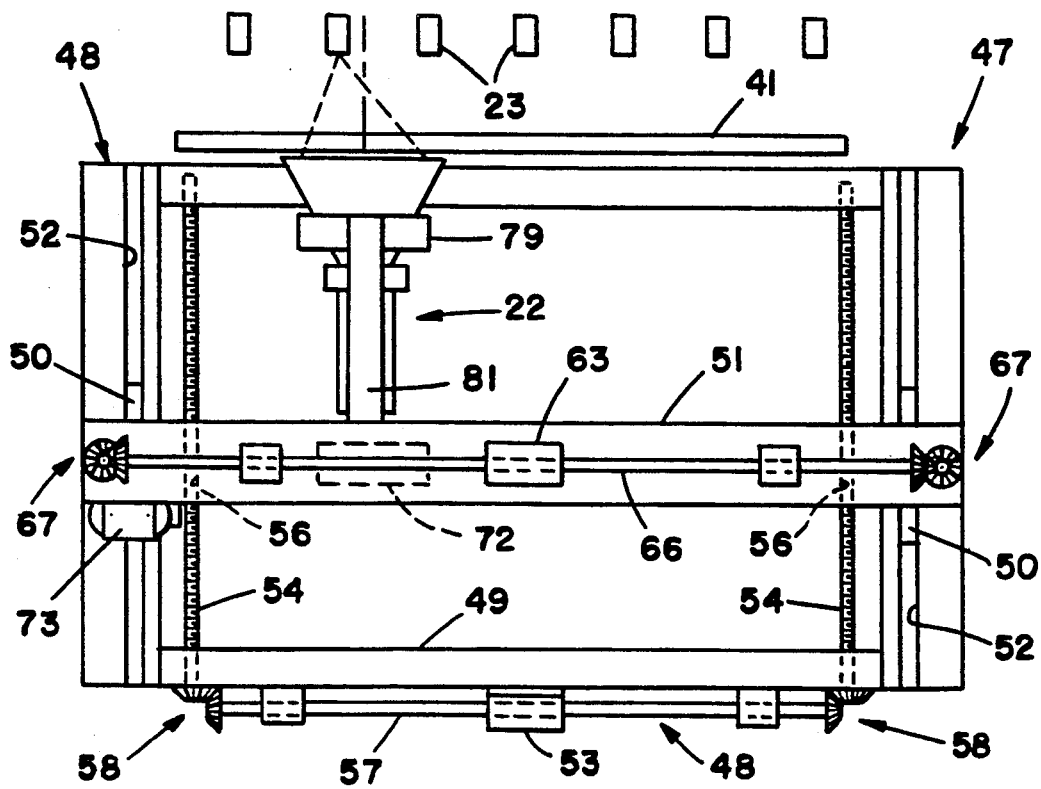
FIG_2
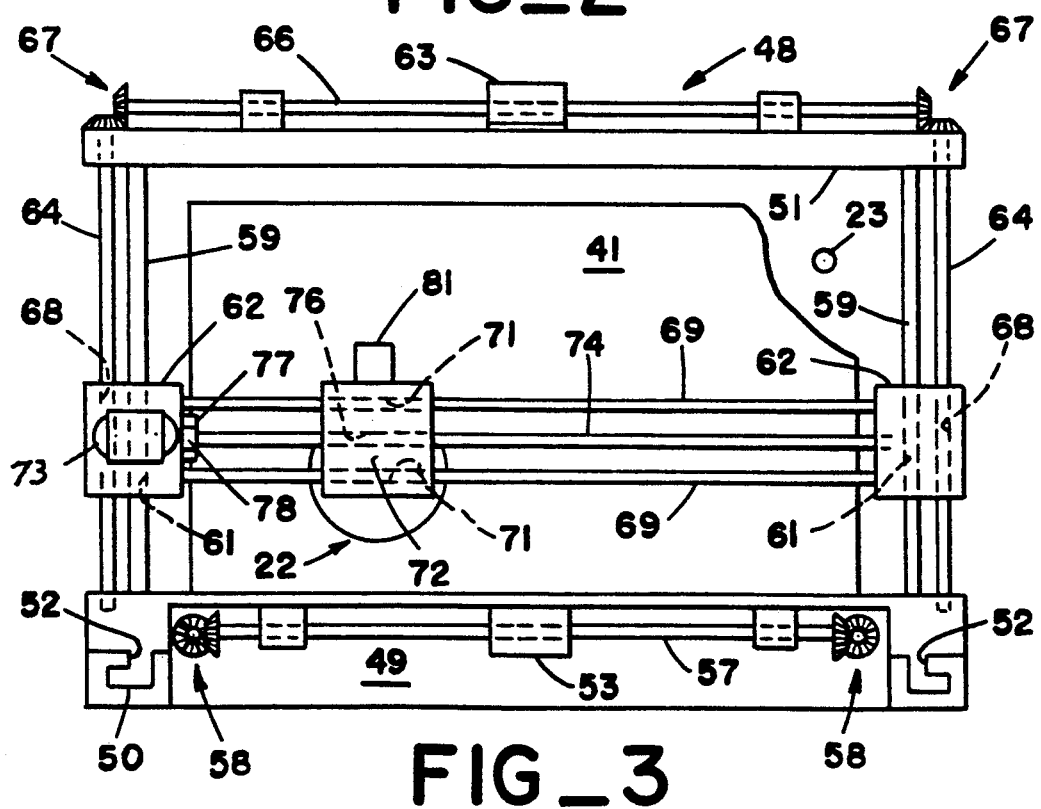
FIG_3

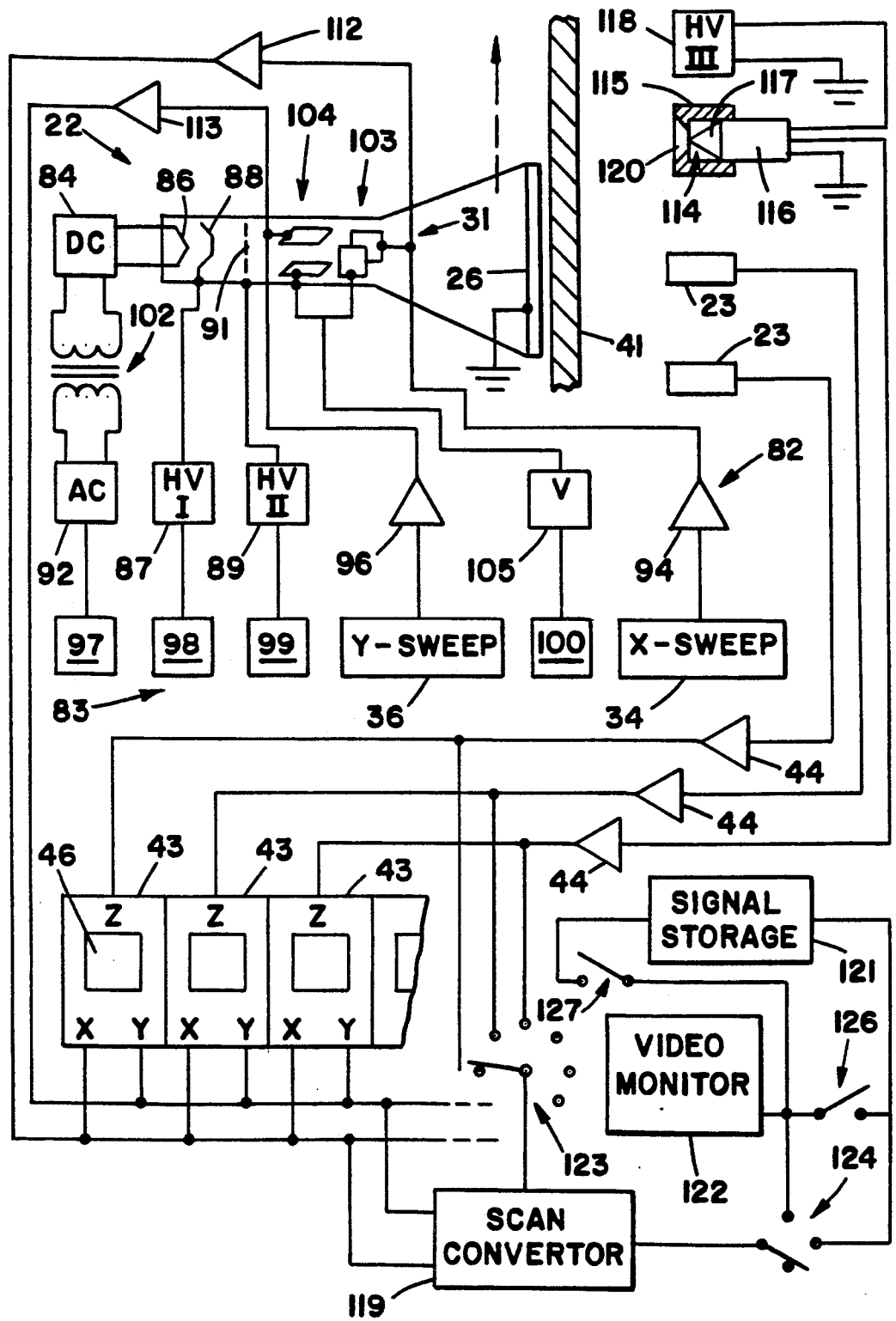
FIG_4

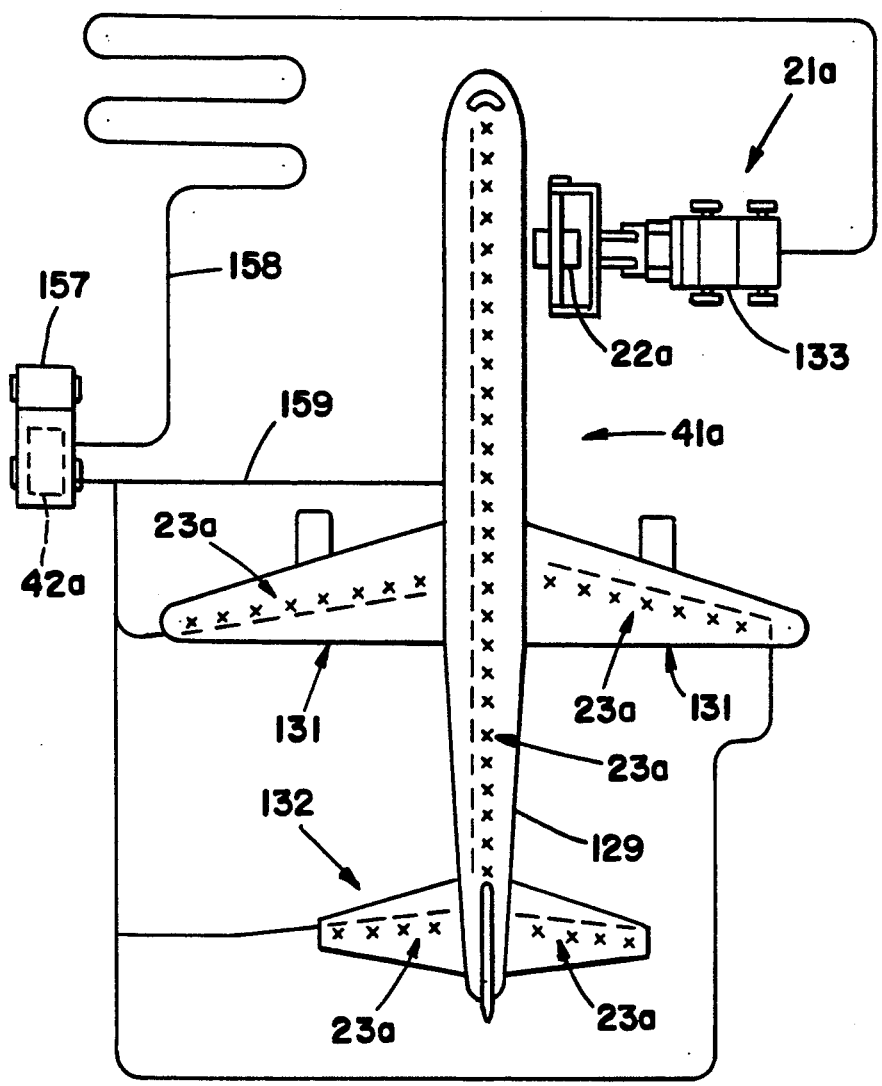
FIG_5
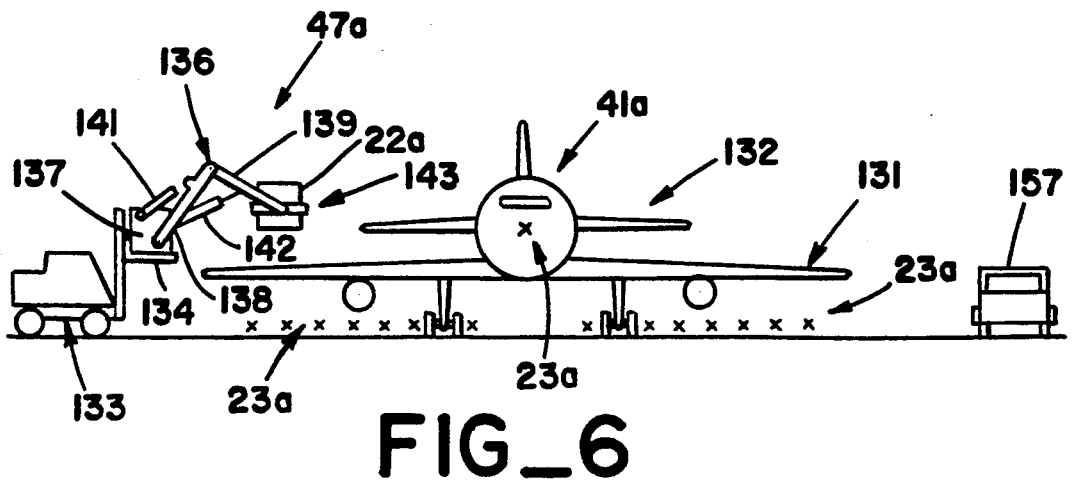
FIG_6

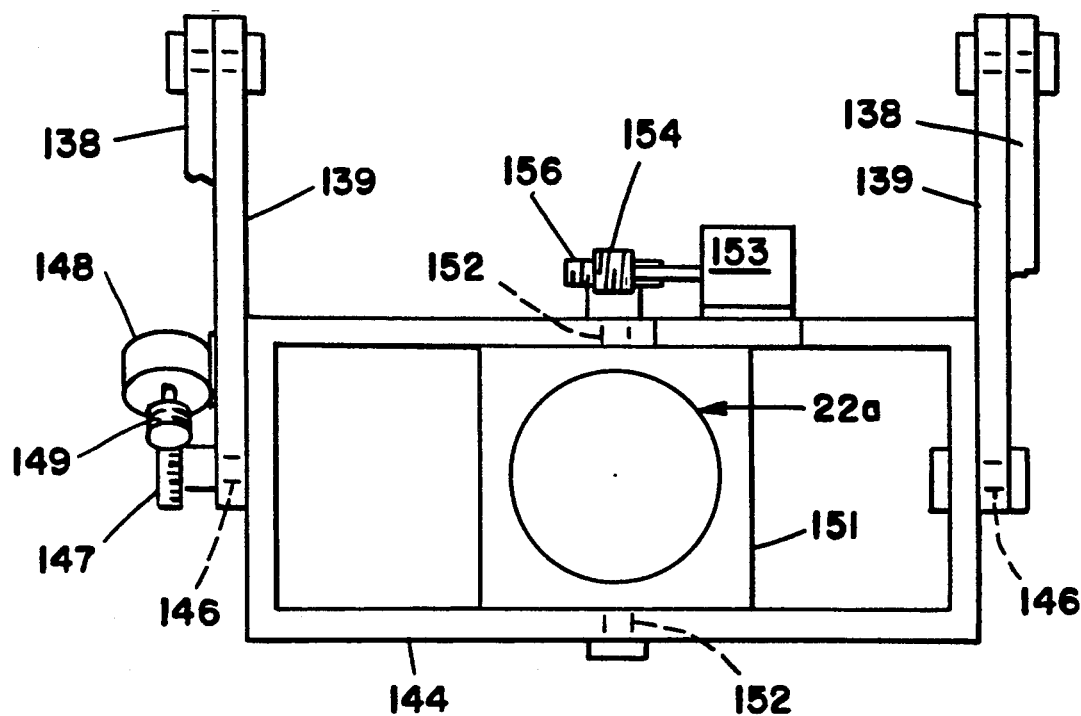
FIG_7
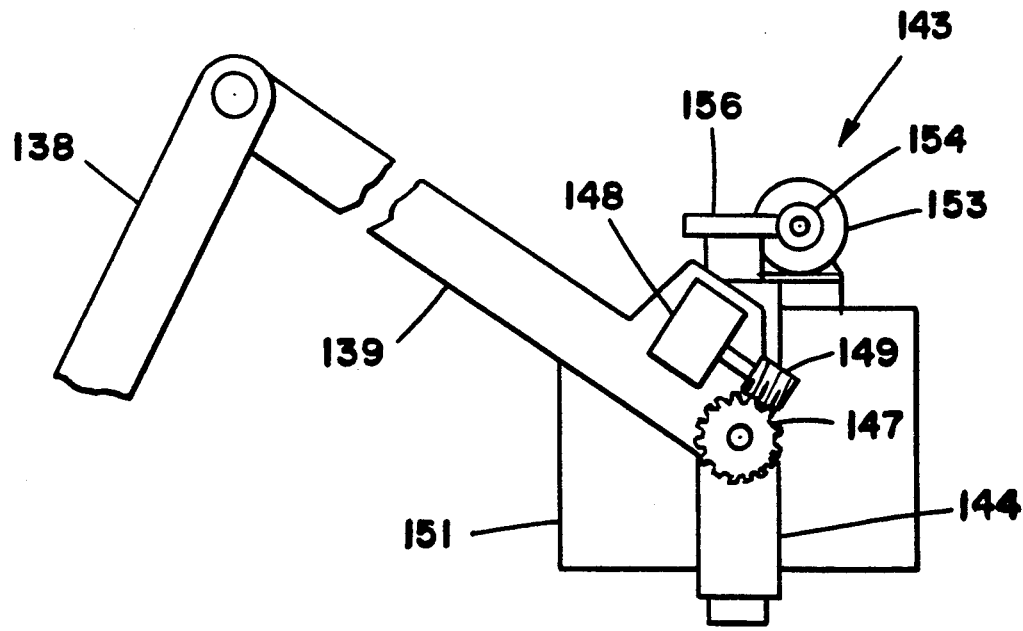
FIG_8

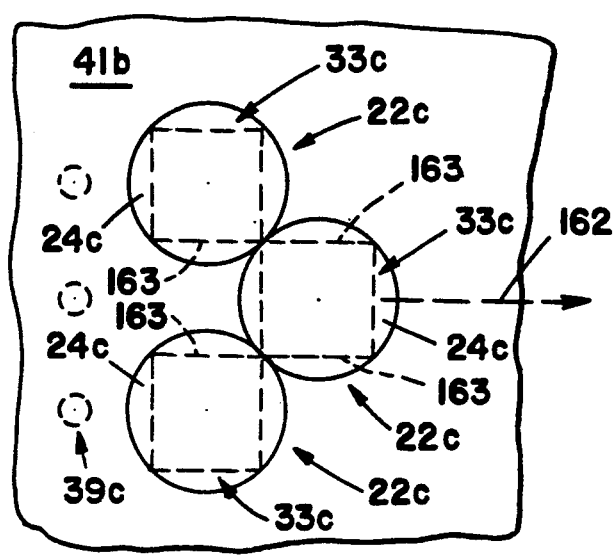
FIG_10
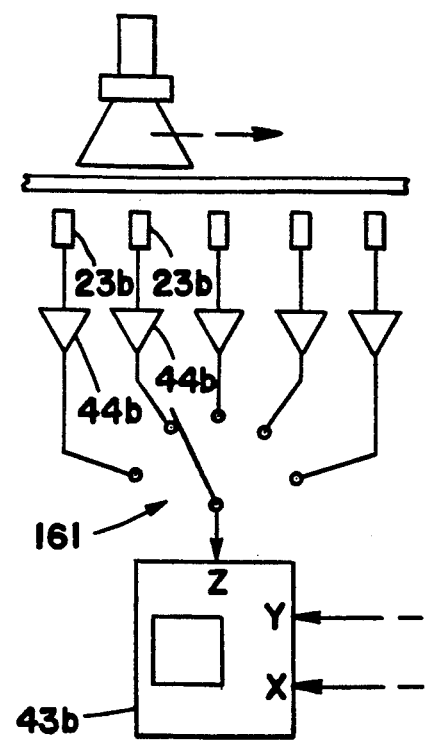
FIG_9
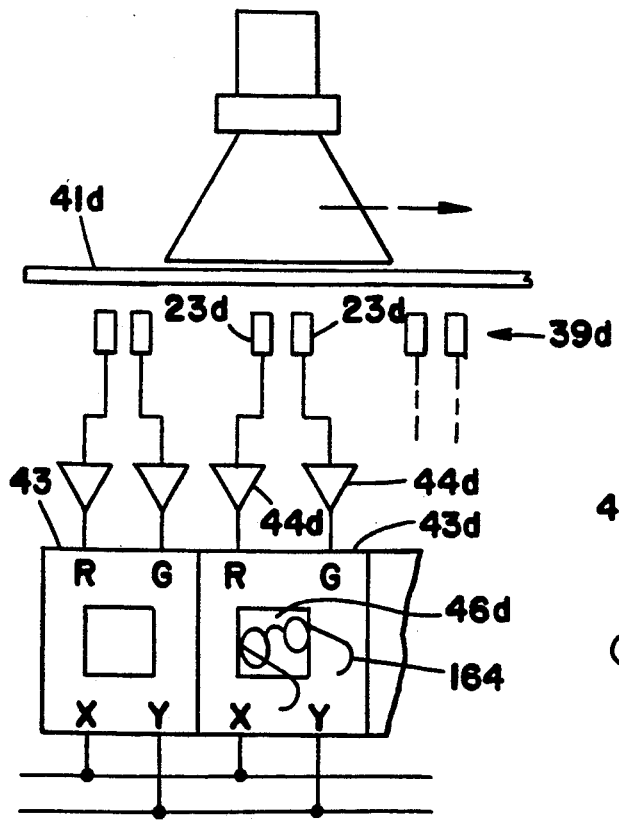
FIG_11
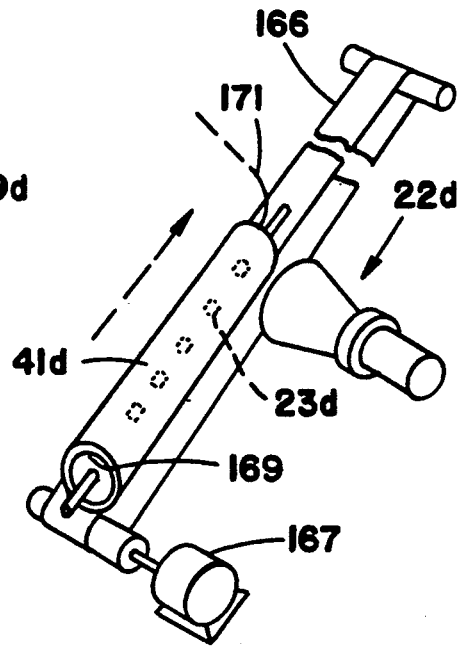
FIG_12

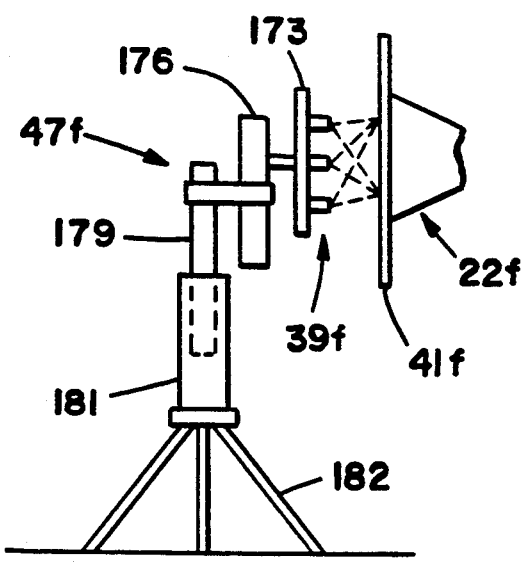
FIG_13
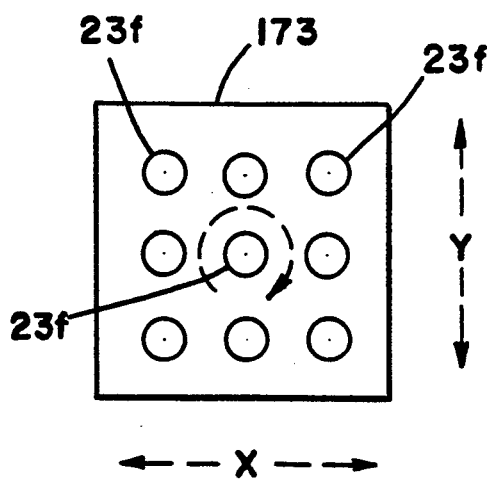
FIG_14
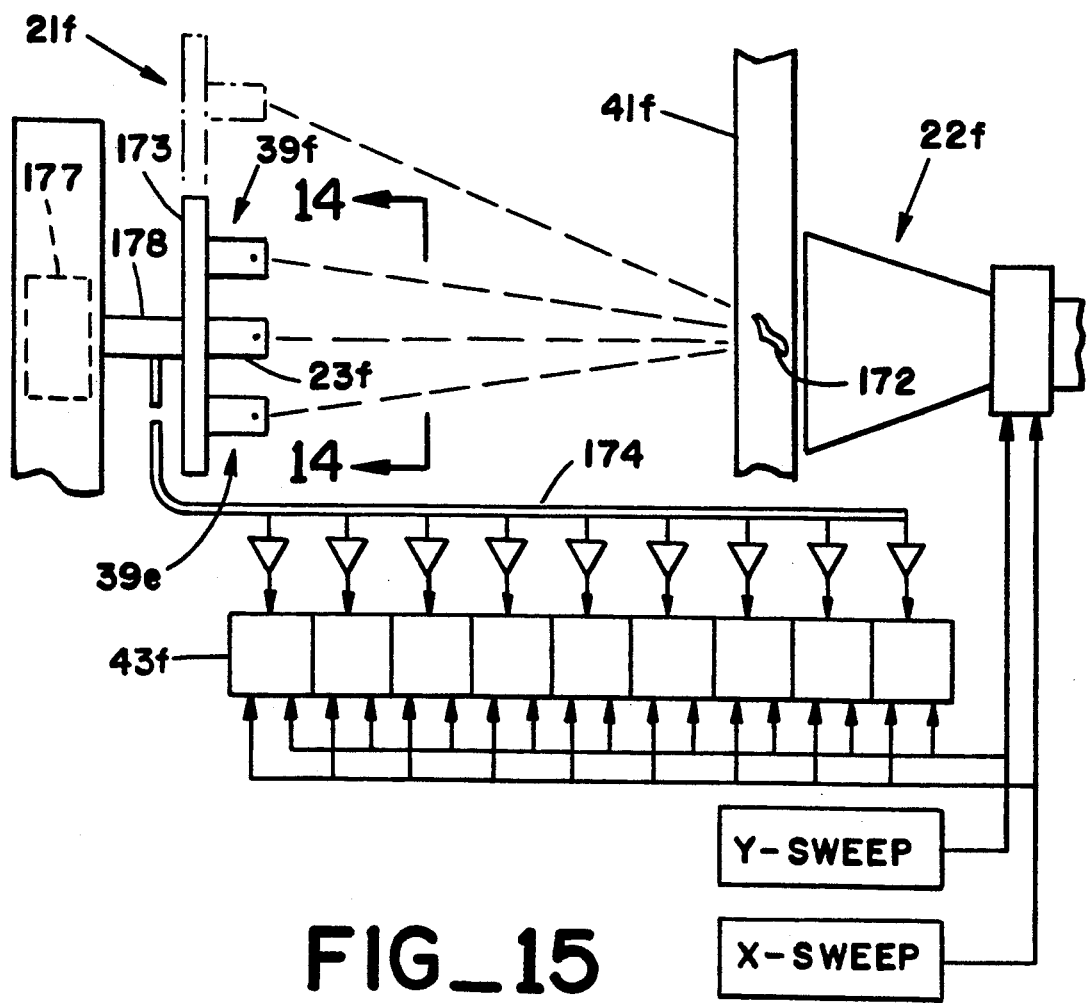
FIG_15

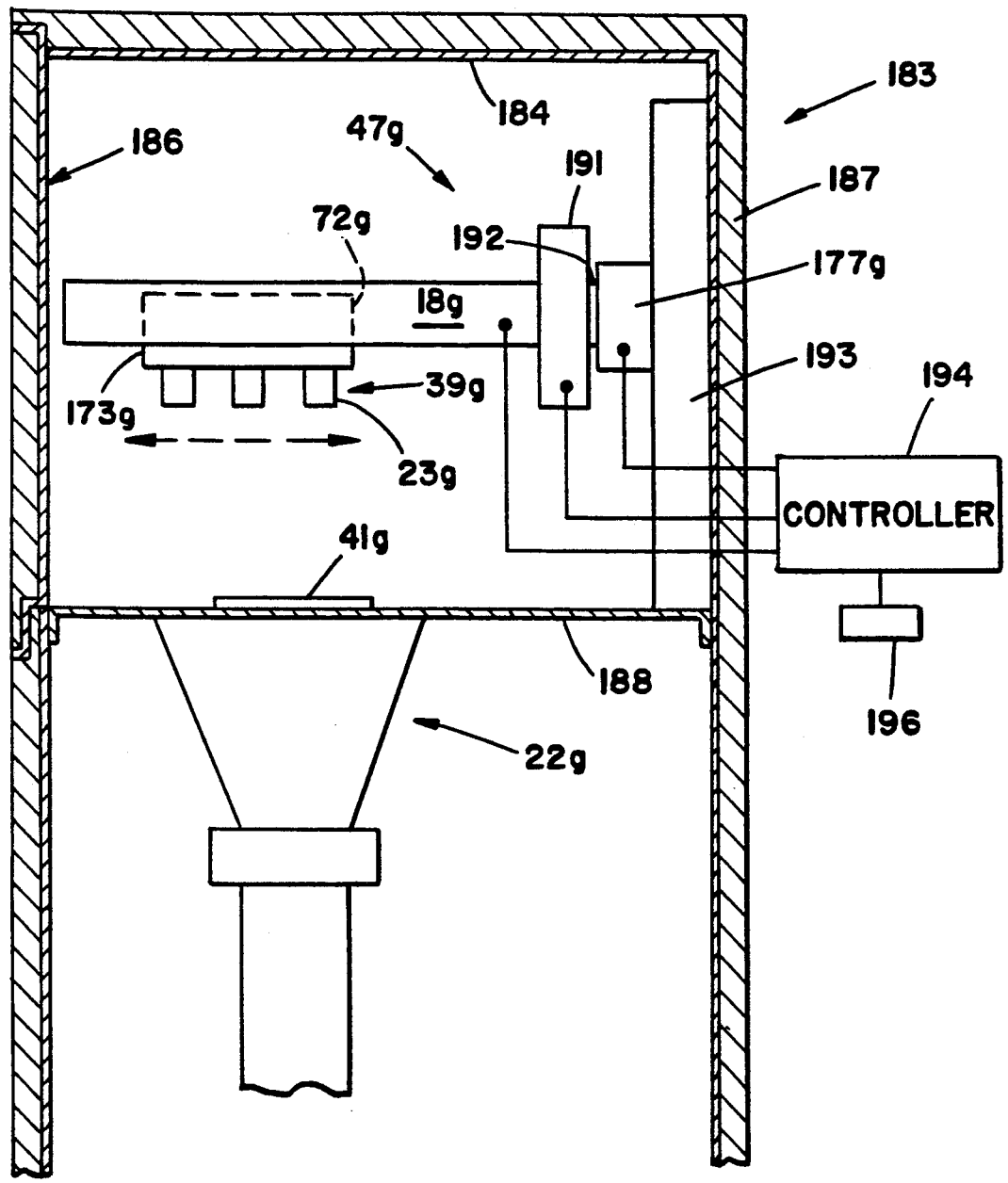
FIG_16

MULTIPLE IMAGE SCANNING X-RAY METHOD AND APPARATUS

TECHNICAL FIELD

This invention relates to radiography and more particularly to methods and apparatus which generate x-ray image data by situating the object that is to be examined between a broad x-ray source and small area x-ray detector and sweeping an x-ray origin point at the source through a raster pattern.

BACKGROUND OF THE INVENTION

The present invention is particularly, but not exclusively, useful for x-ray examination of large objects. The fuselage and wings of aircraft, boat hulls, submarine bulkheads, pressure vessels, fuel tanks and pipelines are examples of objects that may require x-ray inspection to detect internal structural flaws or for other reasons. Prior x-ray systems and procedures are not ideally adapted for radiographic examination of such structures.

In one prior process for x-raying large objects, a point source of x-rays is situated at successive locations along the object in order to expose x-ray film which may be at the other side of the object or within the object. This is an undesirably slow procedure as the film must be removed and developed in order to obtain the desired information. In some cases, an impractically large amount of film may be required.

Another prior process for x-ray inspection of large objects avoids this problem and provides a real time or instantaneous image by replacing the film with an image intensifier type of x-ray detector. Systems of this kind require a precise alignment of the x-ray source and the detector. In some cases the source and detector are secured to a stationary support which holds the two components in the required positions relative to each other while the object undergoing examination travels between them. In other instances, the source and detector are secured to opposite ends of an arm which holds the two components in the required precise alignment while enabling joint movement of the source and detector along the object. The arm typically has a C-shaped configuration in order to reach around the object.

The requirement that the object be traveled between a stationary source and stationary detector or, alternately, that the source and detector be interconnected by a rigid structure makes it impractical or complicated and expensive at best to x-ray many large objects with systems of this kind. Manipulating large objects, such as an aircraft for example, between a stationary source and detector in the necessary manner is not a practical procedure. A C-arm interconnection between the source and detector of sufficient size to enable joint movement of a precisely aligned source and detector along the aircraft would be extremely bulky and costly and difficult to maneuver. In addition, the protruding wings and empennage of the aircraft would restrict the positioning of the apparatus relative to the aircraft.

Considering another example, a lengthy pipe of reasonably small diameter can be x-rayed by a source and imaging detector of the above described kind but the source and detector must be at opposite sides of the pipe as the need for a rigid interconnection between the two components makes it difficult or impossible to situate one component within the pipe. Consequently, internal characteristics of opposite sidewall regions of the pipe are superimposed in the resulting x-ray images and this complicates interpretation of the data.

Thus a system which does not require precise alignment of the x-ray source and x-ray detector and/or a rigid structural interconnection between the two components would be highly advantageous. The size and configuration of the object to be examined would not impose practical restrictions of the above discussed kind on the usages of such a system.

Prior systems of the above discussed kind for x-ray inspection of large objects that are designed to provide high resolution in the images have an undesirably small field of view. The field of view is determined by the size of the detector rather than the size of the x-ray source. The best resolution is obtained by using an array of minute detectors such as charge coupled devices, use of geometric magnification with image intensifiers or x-ray sensitive video cameras. All of these devices have a relatively small field of view. This slows the inspection process as the throughput of image data is a function of the field of view. It would be advantageous if the speed of examination were not determined by detector size.

X-ray examination of objects can be facilitated and made more informative if the x-ray system views the examined object from different angles and provides images corresponding to different viewing angles. Use of the above described prior x-ray imaging systems for this purpose is undesirably complicated as the x-ray source and x-ray detector must be linked by rigid alignment structure and be jointly shifted to different positions or the object itself must be maneuvered into a series of different orientations to obtain a sequence of images taken at different angles.

The present invention is directed to overcoming one or more of the problems discussed above.

SUMMARY OF THE INVENTION

In one aspect, the present invention provides an x-ray scanning system for examining internal characteristics of an object. Components include x-ray source means for scanning a charged particle beam in a raster pattern on a target plate to produce x-rays successively at different small areas of the plate and at least one x-ray detector for disposition at the opposite side of the object from the x-ray source. The detector has an x-ray sensitive area and means for producing an output signal that is indicative of x-rays impinging on the sensitive area. The sensitive area is sufficiently small in relation to the raster pattern of the source to cause the output signals to vary in accordance with variations of x-ray transmissivity at different regions of the object as the charged particle beam is swept in the raster pattern. Traveling means provide for lateral travel of at least one of the x-ray source and the x-ray detector relative to the other during examination of the object. Additional means generate a sequence of different x-ray views of the object taken at successive stages of the lateral travel by correlating variations of said output signal with the position of the charged particle beam in the raster pattern at the time that the variations occur.

In another aspect of the invention, the apparatus includes a plurality of the detectors disposed in spaced apart relationship and forming a detector array and means for generating different sequences of the different x-ray views from the output signals of different ones of the detectors during the lateral travel.

In another aspect, the invention provides a method for examining internal characteristics of an object. Steps in the method include generating x-rays at an x-ray origin point, moving the origin point in a raster pattern and locating the object in the path of x-rays that are emitted from the raster area. X-rays are detected at least at one x-ray detection point in order to produce an output signal that is indicative of variations of x-ray transmissivity within the scanned region of the object. The detection point is sufficiently small in relation to the raster area to cause the signal to vary in response to varying x-ray transmission through successive regions of the object as the x-ray origin point moves through the raster pattern. At least one of the raster area and the detection point is traveled laterally relative to the other during the examination of the object. The output signals that originate at successive locations along the path of travel are used to generate a sequence of different x-ray views of the object.

The invention does not require precise alignment of the x-ray source and a detector and can provide useful data in the presence of a substantial amount of sideward or upward or downward displacement of one component from the other and is tolerant of a substantial degree of difference in angular orientation of the source and detector. Consequently the invention does not necessarily require that the object which is to be examined be traveled between a stationary x-ray source and detector or, alternately, that the source and detector be fastened to each other by rigid connecting structure for the purpose of maintaining a precise alignment. This greatly facilitates x-ray inspection of large objects such as an aircraft as one example. Individual small detectors can be placed at spaced apart locations within or adjacent to the object and a scanning x-ray source may then be traveled and reoriented if necessary to obtain a sequence of two dimensional or three dimensional x-ray views depicting different portions of the object and/or which view the same region of the object from different angles. The system may also be operated by traveling the detector or detector array instead of the x-ray source or by relative movement of both components where the configuration of the examined object makes that desirable. The invention enables a more rapid x-ray examination of sizable objects and may be embodied in a compact, economical and mobile system of components. The invention is not limited to radioscopic examination of large objects and can be used, for example, to produce x-ray images of small objects from different, progressively changing viewing angles.

The invention, together with further aspects and advantages thereof, may be further understood by reference to the following description of preferred embodiments and by reference to the accompanying drawings.

BRIEF DESCRIPTION OF THE DRAWINGS

FIG. 1 is in part a broken out perspective view and in part a schematic circuit diagram depicting certain basic components of an x-ray scanning system for examining internal characteristics of an object.

FIG. 2 is a top view of mechanism for traveling and positioning the scanning x-ray tube of FIG. 1.

FIG. 3 is an elevation view of the mechanism of FIG. 2.

FIG. 4 is a schematic circuit diagram depicting electrical components and interconnections of the system of FIG. 1.

FIG. 5 is is a top view of a second embodiment of the invention shown in the process of performing an x-ray examination of the fuselage, wings and empennage of a large airplane.

FIG. 6 is an elevation view of the embodiment of FIG. 5 with a mobile vehicle component of the system being shown in a changed position.

FIG. 7 is a front view of a portion of the x-ray source traveling and positioning mechanism of the embodiment of FIGS. 5 and 6.

FIG. 8 is a side view of the mechanism of FIG. 7.

FIG. 9 is a schematic circuit diagram showing a modification of the x-ray image generating components of the system.

FIG. 10 depicts a modification of the system which employs a plurality of scanning x-ray tubes to enable a more rapid x-ray inspection of an object.

FIG. 11 is a schematic diagram of another modification of the apparatus which enables production of stereo or three dimensional x-ray image data.

FIG. 12 is a perspective view of another embodiment of the invention in which the object undergoing x-ray examination and an array of detectors are traveled while the x-ray source remains stationary.

FIG. 13 is an elevation view of another embodiment of the invention which is particularly suited for rapidly producing multiple x-ray images of an object at a series of different viewing angles to enhance recognition of structural flaws.

FIG. 14 is a front elevation view of the x-ray detector array of the embodiment of FIG. 13.

FIG. 15 is in part an enlarged view of the upper region of the embodiment of FIG. 13 and in part a schematic circuit diagram showing electrical components.

FIG. 16 is an elevation section view depicting a shielded cabinet x-ray installation embodying the invention and which is adapted for x-ray examination of relatively small objects such as electronic circuit boards.

DETAILED DESCRIPTION OF THE PREFERRED EMBODIMENTS

Referring initially to FIG. 1 of the drawings, an x-ray scanning system 21 embodying the invention includes x-ray source means 22 and x-ray detectors 23 which may be of the type described in my prior U.S. Pat. No. 3,949,229 issued Apr. 6, 1976 and entitled "X-ray Scanning Method and Apparatus" which patent is hereby incorporated by reference. X-ray source means 22 of this kind have an evacuated envelope or tube 24 with a face which includes a target plate 26 formed of thin x-ray transmissive metal. A charged particle beam 27, from an electron gun 28 in this example, is directed towards plate 26 to generate x-rays at an origin point 29. Beam deflection means 30, which includes electrostatic deflection plates 31 in this example, repetitively deflects the charged particle beam 27 along a series of parallel scan lines 32. This causes the x-ray origin point 29 to scan through a sizable raster pattern 33 at target plate 26. The scan lines 32 are typically greater in number and more closely spaced than can be depicted in FIG. 1. An x-axis sweep frequency generator 34 and lower frequency y-axis sweep frequency generator 36 provide cyclical voltages to the deflection plates 31 in the known manner to produce the raster pattern 33.

The system 21 employs x-ray detectors 23 which have a radiation sensitive area 38 that is very small, preferably point like, in relation to the size of the raster pattern 33. In the present embodiment of the invention, an array 39 of such detectors 23 is disposed on the opposite side of the examined object 41 from the scanning x-ray source 22 in position to detect x-rays that pass through the object. The sensitive areas 38 of the detectors 23 are spaced apart along the object 41 preferably by distances which do not exceed the expanse of raster pattern 33. When the spacing is greater some areas of the object can only be viewed obliquely. The spacing of the sensitive areas 38 may, if desired, be greater than the extent of the raster pattern 38 if the detectors 23 are spaced from the object 41 by a greater distance than the spacing of the source 22 from the object.

A single row of detectors 23 may be used to examine all portions of the object 41 if the object has a height or width that is no larger than the height and/or width of raster pattern 33. If this condition is not met, the array 39 may include plural rows of detectors 23 having sensitive areas 38 that are spaced as described above.

The system 21 further includes means 42 for generating a sequence of different x-ray views of the object 41 at successive stages of travel of the x-ray source 22 along the object and the detector array 39. Alternately, the object 41 and detector array 39 may be jointly traveled past a stationary x-ray source 22 or an x-ray source that is traveled at a different rate or which travels in an opposite direction.

The x-ray view generating means 42 constructs images essentially by correlating variations of the output signal from each detector 23 with the position of the charged particle beam 27 and x-ray origin point 29 in raster pattern 33 at the times that the variations occur. In this example means 42 includes a series of cathode ray tube visual displays or monitors 43 of the known type which scan a point of light in a raster pattern in response to X axis and Y axis sweep frequency signals while modulating intensity of the point of light in accordance with a variable Z axis signal. The monitors 43 may be oscilloscopes preferably of the adjustable persistence or storage type. Standard oscilloscopes can also be used and the images can be stored for further analysis by photographing the oscilloscope screen. The monitors 43 may also be commercial television sets if the sweep and intensity control signals are processed through a video scan converter and signal storage.

Preferably, a separate monitor 43 is provided for each detector 23 although this is not essential as will hereinafter be described in more detail. Each monitor 43 receives the same X and Y sweep frequency signals that are applied to the x-ray source 22 and thus the raster pattern of each monitor is similar to and synchronized with the raster pattern 33 of the source. Each monitor receives a Z or intensity control signal from a separate detector 23 through a separate one of a series of signal amplifiers 44. Thus any detector 23 which is currently receiving x-rays emanating from the moving origin point 29 produces an electrical output signal voltage that varies during the course of each raster scan in accordance with variations of x-ray transmissivity in the region of object 41 through which the detected x-rays pass. This produces an image on the screen 46 of the associated monitor 43 in which areas of differing x-ray transmissivity in the object 41 can be visually identified by differences in brightness in the image.

X-rays are emitted from origin point 29 in all directions throughout a wide angle having an apex at the origin point. Consequently, it is not necessary that the x-ray source 22 and a detector 23 be in precise alignment along a single centerline in order to produce an x-ray image. If source 22 is offset laterally or upwardly or downwardly from a detector 23, the detector can still produce a useful image although it depicts the scanned region as viewed at an angle. Detectors 23 which are a considerable distance away from the x-ray source 22 at a particular time may not produce a meaningful image at that time as the paths which x-rays must travel to reach those detectors may be so angled relative to object 41 that the object completely absorbs such x-rays.

For purposes of an initial example, the examined object 41 has been depicted as being a flat plate of uniform thickness. Objects 41 of this shape can be examined by traveling the x-ray source in one direction indicated by dashed arrow X in FIG. 1 and in an orthogonal direction as indicated by arrow Y. Travel along only a single direction is possible if the object 41 has a height or width that does not exceed the height or width of raster pattern 33. Preferably the x-ray source 22 is also arranged to be retractable away from object 41 in a third orthogonal direction indicated by arrow Z. Moving the source 22 outward from the object 41 causes the region of the object which is being imaged at monitor screens 46 to be magnified as the size of the raster patterns at the screens does not change. As will hereinafter be described in more detail, the x-ray source 22 may also be supported in a tiltable and swivelable manner if objects having curved surfaces are to be examined.

Referring jointly to FIGS. 2 and 3, means 47 for traveling the x-ray source 22 in the above described manner in this particular embodiment includes an X-Y-Z table 48 of the type that provides for motor controlled positioning of an object at any selected locations along three mutually orthogonal axes.

Such a table 48 may, for example, have a base 49 which is a horizontally oriented rectangular framework. An upright rectangular second frame 51 has angled shoes 50 that ride in angled grooves 52 in the side portions of the base 49 enabling sliding movement of the second frame towards the examined object 41 and away from the object. This movement is produced by a Z-axis electrical motor 53 which is secured to the back of base framework 49. A pair of lead screws 54 extend between the front and back portions of the base framework 49 at opposite sides of the framework and through bores 56 in the lower portion of second frame 51 which bores have threads that engage with the lead screws. Motor 53 turns a shaft 57 which in turn rotates both lead screws 54 through sets of bevel gears 58 which couple the shaft to the lead screw. Thus operation of motor 53 in one direction advances the second frame 51 towards the examined object 41 and reversal of the motor retracts the second frame away from the object.

To enable movement in the vertical or Y direction, the upright side portions of second frame 51 are shafts 59 each of which extends through a bore 61 in a separate one of a pair of slider blocks 62 that may be traveled upward and downward along the shafts. The vertical motion is produced by a Y-axis electrical motor 63 secured to the top of frame 51 and which turns another pair of lead screws 64 through a shaft 66 and additional bevel gear sets 67. Lead screws 64 extend through and engage in threaded bores 68 in slider blocks 62. Thus operation of motor 63 jointly travels blocks 62 upward or downward depending on the direction of motor operation.

To provide for X-axis motion, in a horizontal direction that is parallel to the plane of the examined object 41, a pair of spaced apart rods 69 extend between slider blocks 62 and through bores 71 in a carriage 72 that is slidable along the rods. The carriage 72 is traveled by an X-axis electrical drive motor 73 that is secured to the back of one of the slider blocks 62. Another lead screw 74 extends between the slider blocks 62 and engages carriage 72 within a threaded bore 76 in the carriage, motor 73 being coupled to the lead screw by a set of gears 77 and 78.

Referring to FIGS. 1, 2 and 3 in combination, the x-ray source 22 is secured to carriage 72, in the present example by a ring 79 which clasps the x-ray source tube 24 and an angled arm 81 that extends to the carriage and which is secured to the carriage. Thus the x-ray source 22 may be traveled relative to the examined object 41 and detector array 39 in any of three mutually orthogonal directions by selective operation of motors 53, 63 and 73. Switches (not shown) for actuating and deactuating the motors 53, 63 and 73 are preferably located together to facilitate operator control of the movement of the x-ray source 22.

Referring again to FIG. 1 in particular, x-ray images can be produced and interpreted by an observer while the x-ray source 22 moves continuously along a row or successive rows of the detectors 23. As this results in a continuously changing viewing angle, it is preferable in many cases to travel the x-ray source 22 in a stepped manner in which motion of the source is temporarily stopped at successive locations along the examined object 41. Under either mode of operation, the images of primary interest appear progressively at successive ones of the monitors 43.

Referring to FIG. 4, the circuits 82 that provide operating voltages and currents for the scanning x-ray source 22 are preferably of the known programmable type which vary the voltages and currents in response to digital or analog signals from controllers 83 that may be situated at a remote location. Such circuits in this embodiment include a direct current supply 84 which applies heating current to the filament 86 of source 22, a first high voltage supply 87 which applies a high negative voltage to the cathode 88 of the source, a second high voltage supply 89 that applies a less negative and adjustable voltage to the control grid 91 that regulates the magnitude of the electron beam current that originates at the heated cathode 88 and X and Y sweep frequency amplifiers 94 and 96 respectively which apply the sweep frequency signals from generators 34 and 36 to the beam deflection plates 31.

The remotely located controllers 83 which enable operator adjustment of voltages and currents at the source 22 include a filament current controller 97, a high voltage controller 98, a control grid bias controller 99, reflection plate bias controller 100 and the X-sweep frequency and Y-sweep frequency generators 34 and 36. Controllers 83 produce selectable control signal voltages if the source control circuits 82 are of the analog type that respond to variable voltages. Preferably circuits 82 are of the type that respond to digital signals in which case the controllers 83 produce digital signals. The controllers 83 are not necessarily physically separate components if circuits 82 respond to digital signals as the functions of each of the controllers can be performed by a computer.

As the high voltage for electron beam acceleration is applied to the cathode 88 end of the x-ray source 22, the target plate 26 which is the anode may be grounded. This prevents electrical arcing between the source 22 and the examined object 41. As the cathode 88 region is at high voltage, the D.C. filament current supply 84 receives A.C. operating current from a programmable A.C. source 92 through an isolation transformer 102.

The X and Y sweep frequency voltages from amplifiers 94 and 96 are repetitive ramp waveforms of different frequency that are applied to one of the pair of X deflection plates 103 and one of the pair of Y deflection plates 104, the other plate of each pair being connected to a D.C. voltage supply 105 that provides a selectable voltage that is intermediate between the high voltage at control grid 89 and ground. The sweep frequencies are also transmitted to the X and Y sweep frequency terminals of the monitors 43, through additional amplifiers 112 and 113, to synchronize the raster scans of the x-ray source 22 and the monitors.

The detectors 23 of this example of the invention are of the known type which have a small scintillation crystal 114 of sodium iodide or the like that emits light in response to intercepted x-rays. The crystal 114 is optically coupled to a photomulipler tube 116 by a light pipe 117. A third high voltage supply 118 energizes the tubes 116 each of which transmits an intensity control voltage to the associated amplifier 44 and monitor 43 in response to x-rays which are intercepted by the crystal of the detector. Other types of detector, such as photodiodes, ion chambers or charged coupled devices for example may also be used.

Cup shaped collimator shields 115 formed of radiation absorbent material such as lead may be fitted on the regions of the detectors 23 at which the x-ray sensitive crystals 114 are located in order to intercept scattered x-rays or stray radiation. An aperture 120 in the face of the collimator 115 allows x-rays from source 22 to reach the scintillation crystal 114. Aperture 120 may be broadly tapered to enable the generation of image data by a detector 23 when it is offset from the source 22 as well as at times when the source 22 and the detector are in alignment. The collimator shields 115 can be eliminated in instances where detectors 23 need to respond to x-rays that arrive at high angles.

The image data contained in the X and Y sweep frequency signals delivered by amplifiers 112 and 113 and the detector output amplifiers 44 can be utilized in a variety of ways additional to or in place of the generation of real time images at the screens 46 of monitors 43. For example, as shown in FIG. 4, the sweep frequency signals and any selected one of the detector output amplifier signals can be processed through a video scan converter 119 and be recorded in a video signal storage 121 for later viewing on a video monitor 122. A multiposition switch 123 enables selection of the particular detector signal that is to be stored at any given time. Another switch 124 has a first position at which the output of scan converter 119 goes only to signal storage 121 and a second position at which the scan convertor output goes to video monitor 122 for real time viewing of the image. Another switch 126 is connected between the inputs of monitor 122 and storage 121 to enable concurrent viewing and storage of the scan converter output. An additional switch 127, connected between the output of the storage 121 and monitor 122 enables monitor display of previously stored image data.

Components of the x-ray scanning system can take a variety of different forms and be arranged in a variety of different ways depending on the nature of the objects which are to be examined and the circumstances under which the examinations are conducted. Referring jointly to FIGS. 5 and 6, another embodiment of the invention is shown that is particularly adapted for detecting structural defects in aircraft including a very large airplane 41a.

In this example, a row of spaced apart detectors 23a extends along the centerline of the fuselage 129 of the airplane 41a and one or more additional rows are disposed beneath each wing 131 and also below each side of the tail assembly 132 of the plane. The detectors 23a may be temporarily installed within or adjacent the airplane 41a or may be built-in permanent components within the wings, fuselage and other structures of the aircraft in order to facilitate periodic x-ray inspections. The x-ray source 22a is carried on a powered vehicle 133 which functions as a component of the means 47a for traveling the source relative to the array of detectors 23a. The vehicle 133 may, for example, be a lift truck of the known type which has load carrying forks 134 that may be selectively raised and lowered. The forks 134 enable up and down or Y-axis travel of the source 22a. Maneuvering of the vehicle 133 itself enables horizontal X-axis movement of the source 22a in a direction parallel to the rows of detectors and also Z-axis movement towards and away from the detectors.

The source traveling means 47a preferably enables additional traveling of source 22a in the Z-axis direction relative to the vehicle 133. This enables the source 22a to be moved to successive circumferential positions around fuselage 129 and successive positions above wings 131 and tail assembly 132 while the vehicle is parked at a particular location. For this purpose, the source 22 is disposed at the end of linkage 136 which can be extended from vehicle 133 and retracted towards the vehicle. A housing 137 is supported by and secured to the lift truck forks 134. Linkage 136 includes a first pair of parallel arms 138 which are pivoted to housing 137 and a second pair of parallel arms 139 pivoted to the opposite ends of arms 138 and which carry the x-ray source 22a. A first pair of hydraulic actuators 141 of the extensible and contractable type are connected between housing 137 and arms 138 to enable powered pivoting of arms 138 in upward and downward directions and a second pair of hydraulic actuators 142 are connected between arms 138 and 139 to provide for upward and downward pivoting of arms 139 relative to arms 138.

Thus actuators 141 and 142 enable the source 22a to be selectively traveled outward from vehicle 133 and to be retracted back towards the vehicle in order to position the source 22a at different locations above or below airplane 41a. The linkage 136 may also be used to effect upward and downward motion of the source 22a additional to that provided for by the forks 134 of vehicle 133.

Airplane 41a differs from the examined object of the first described embodiment in that the airplane has curved surfaces and angled surfaces. In order to maintain x ray source 22a in facing relationship with one or more of the detectors 23a as it is traveled to successive different locations around the airplane 41a, additional means 143 enable selective tilting and swiveling movement of the source about horizontal and vertical axes respectively. Referring to FIGS. 7 and 8 in conjunction, such means 143 in this example includes a rectangular frame 144 situated between the ends of linkage arms 139 and which is coupled to the arms by pivot axles 146 which extend from the frame and which enable the frame to be turned about a horizontal axis of rotation. One of the axles is formed with a gear 147. A rotary hydraulic motor 148 is secured to the adjacent arm 139 and turns a worm gear 149 which engages gear 147 to effect upward or downward tilting of frame 144.

The x-ray source 22a is disposed in a rectangular housing 151 which extends through the middle of frame 144. Housing 151 has vertically directed pivot axles 152 that extend through the center of the upper and lower portions of frame 144 to couple the housing to the frame while enabling swiveling of the housing and source 22a about an axis that is othogonal to the tilting axis. Angular turning of the housing 151 and source 22a about the swivel axis is effected with another reversible rotary hydraulic motor 153 which is secured to frame 144. Motor 153 turns a worm gear 154 that engages another gear 156 on the end of the uppermost pivot axle 152.

Referring again to FIGS. 5 and 6, the x-ray source 22a, detectors 23a and the control circuits and image generating means 42a of the aircraft examining system 21a may be similar to the corresponding components of the first described embodiment and operate in a similar manner. If the system 21a is a permanent installation to which airplanes 41a are brought for inspection, the control circuits and image generating means 42a may be situated in a building. In this particular example, which is fully field mobile, the control circuits and image generating means 42a are carried in another mobile vehicle such as a van 157. A first flexible multi-conductor cable 158 provides the hereinbefore described electrical connections between the x-ray source 22a and the control circuits and image generating means 42a and a second similar cable 159 connects the detectors 23a and those components. In some instances, the control circuits and image generating means may be carried on the same vehicle 133 that travels the x-ray source 22a. It is also possible to eliminate the cables 158 and 159 by utilizing radio transmission of control signals and x-ray image data.

An advantage of the system 21a relative to older apparatus for obtaining x-ray views of large objects 41a is that the detectors 23a need not be moved concurrently with movement of the x-ray source 22a to maintain precise alignment. The wide angle field of view of the present system enables images to be generated while the source 22a is offset from the detector 23a that is producing the image or is oriented at a different angle. The entire fuselage 41a may be inspected for defects if the detectors 23a are sufficiently closely spaced that at least one detector intercepts x-rays at each successive relocation of the source 23a along the fuselage.

Referring to FIG. 9, the previously described embodiments of the invention have a separate monitor 43b for each detector 23b. This aids the viewer of the images in tracking the current location at which the data is being originated. It is also possible to use a single monitor 43b or to reduce the number of monitors that are needed. The output amplifiers 44b of all detectors 23b or of a group of the detectors may be coupled to the Z or intensity signal input of a single monitor 43b through a multi-position switch 161. Switch 161 enables operator selection of the particular image that is to be viewed at any given time.

Referring to FIG. 10, throughput of the desired x-ray image data can be increased by jointly traveling a plurality of the scanning x-ray sources 22c along the examined object 41c or by traveling the detector array 39c relative to such a group of sources. The raster patterns 33c of such sources 22c are typically somewhat smaller than the faces of the source vacuum tubes 24c. In order to scan all portions of the object 41c, alternate ones of the plural sources 22c may be offset from the others of the sources in the direction 162 of joint travel of the sources. This enables an overlapping of each source 22c with the adjacent sources to align the adjacent boundaries 163 of the raster patterns 33c of each overlapped pair of sources.

Referring to FIG. 11, three dimensional or stereo imaging of the examined object 41d is possible if the detector array 39d includes one or more spaced apart pairs of detectors 23d, the spacing of the pair from each other being smaller than the spacing of successive ones of the pairs in instances where more than one pair is used. The output amplifier 44d of one member of each pair may be coupled to the red signal input terminal of a monitor 43d of the known type that produces color images while the output amplifier of the other detector of the pair is coupled to the green signal input terminal of the monitor. The observer views the monitor screen 46d through eyeglasses 164 which have one lens that transmits red light only while the other lens transmits green light only. As the red and green images are views taken from a slightly different angle and each image is transmitted to one eye only, the observer perceives the internal structure of object 41d three dimensionally. The monitors 43d can also be of the known type that present differently polarized images to each of the viewer's eyes when viewed through eyeglasses that having differently polarized right and left eye lenses.

In the previously described embodiments of the invention, the x-ray source is traveled along a stationary array of detectors. It is sometimes more convenient to travel the detectors and the object along a stationary x-ray source. Referring to FIG. 12, for example, lengths of pipe 41e can be inspected for flaws using a conveyer belt 166 driven by a motor 167 to carry the pipes past a stationary scanning x-ray source 22e of the hereinbefore described kind. The detectors 23e may be attached to a rod 168 which extends along the centerline of the pipe 41e and which is held in place by circular disks 169 that fit into the pipe. A flexible multi-conductor cord 171 extends out of pipe 41e to enable the previously described electrical connections to the detector. Inspection of all portions of the pipe 41e can be made by turning the pipe about its centerline between repeated passages of the pipe along the source 22e.

Directions of relative travel of the x-ray source and detector array in the previously described embodiments include translation in any of three orthogonal directions, tilting movement and swiveling movement. Referring jointly to FIGS. 13, 14 and 15, perception of internal cracks or voids 172 in the examined object 41f can be enhanced if the detector array 39f is also rotatable as a whole about an axis that is normal to the plane of the detector array.

Cracks or voids 172, other than spherical voids, become more perceptible when paths of the x-rays that generate the image extend along the length of the crack rather than at right angles to the crack. The crack 172 becomes increasingly more perceptible as the angling of the x-ray paths relative to the long dimension of the crack 172 decreases. Thus it is helpful if the system 21f facilitates viewing of the same region of the object 41f at different angles. Rotating an array 39f of the detectors 23f about an axis that extends from the array towards the scanning x-ray source 22f accomplishes this result by concurrently generating images taken from different viewing angles and by enabling progressive changing of the viewing angles of the concurrent images.

In the present example, a rectilinear array 39f of nine spaced apart detectors 23f is secured to a support plate 173, the detectors being in parallel relationship and being directed outward from the plate to receive x-rays from a scanning x-ray source 22f which may be similar to the sources of the previously described embodiments. A multi-conductor cable 174 connects the detectors 23f to separate ones of a series of image display monitors 43f to produce x-ray images of the examined object 41f in the manner which has been hereinbefore described. Cable 174 is flexible to enable at least 90° of angular turning of support plate 173 about the centerline of the central detector 23f. In instances where continued rotation of the detector array 39f may be useful, cable 173 may connect with the array through sliding rotary contacts.

Means 47f for traveling the detector array 39f relative to the x-ray source 22f includes an X-Y table 176 which enables selective horizontal and vertical translation of a motor 177 in directions that are parallel to the face of x-ray source 22f. Motor 177 is an angular positioner of the known type which has an output shaft 178 that turns to any desired angular position in response to position signals. The detector support plate 173 is secured to the end of shaft 178 at the center of the plate. As shown in FIG. 13 in particular, the X-Y table 176 is attached to the upper end of a rod 179 that extends upward from a cylinder 181 that is in turn supported by a tripod 182. Rod 179 is preferably extendable and retractable relative to cylinder 181 to increase the range of vertical positioning of the detector array 39f. While the X-Y table 176 can be of the form hereinbefore described, modular assemblies of positioning apparatus similar to that shown in FIGS. 13 and 15, which include an X-Y table 176, angular positioner motor 177 and a motor driven extendable and retractable support rod 179, are available commercially. Modular positioner components of this kind are marketed by Anorad Corporation of Hauppauge, N.J., U.S.A. under the trademarks ANORIDE and ANOROUND.

The detectors 23f may be activated one at a time or simultaneously to provide up to nine different images representing different viewing angles. Preferably the center detector 23f is positioned at the location of the defect 172 that is to be inspected. Rotation of the detector array 39f, by motor 177, provides a complete set of azimuthal viewing directions as the images are then repeated if turning of the array is continued. This data is sufficient to determine the approximate orientation of the crack 172 that is to be inspected. X-Y table 176 is then used to translate the detector array 39f to the exact detector 23f location at which the best imaging of the crack is attainable.

The number of detectors 23f in the array may be varied and the system is operable with a single detector. Use of plural detectors enables a more rapid inspection of a crack 172 or other defect.

Referring to FIG. 16, a somewhat similar assembly of components can be utilized in a shielded cabinet 183 x-ray imaging facility in which the objects 41g to be inspected may be small objects such as electronic circuit boards. The cabinet 183 has a wall 184 and access door 186 that are covered with shielding material 187 such as lead to prevent the escape of x-rays. A scanning x-ray source 22g similar that which has been previously described is situated below an x-ray transmissive platform 188 on which the examined objects 41g are placed. The detector array 39g in this example is similar to the array previously described with reference to FIGS. 13, 14 and 15 and thus has nine spaced apart detectors 23g secured to a support plate 173g and which in this instance are directed downward to receive x-rays from the source 22g. Other embodiments may have a different number of detectors 23g including only a single such detector. Means 47g for traveling the detector array 39g include an X-Y-Z table secured to wall 186 of the cabinet 183 and which is of the type that provides for motor driven translation of an object in any of three mutually orthogonal directions. In particular, detector support plate 173g is attached to the movable carriage 72g of an X-axis linear slide 189 which extends horizontally. X-axis slide 189 is itself the movable carriage of a Y-axis linear slide 191 that extends horizontally in an orthogonal relationship with slide 189. Y-axis slide 191 is secured to the output shaft 192 of a motor 177g of the previously discussed type that turns the output shaft 192 to a selected angular orientation in response to position signals. Motor 177g is the movable carriage of an upright Z-axis linear slide 193 that is secured to the wall 186 of the cabinet 183. Modular components for providing the above described motions are marketed by the hereinbefore identified Anorad Corporation and can be operated by a digital computer controller 194 coupled to an operator's keyboard 196. The controller 194 enables programming of any desired pattern of movement into the system. Alternately, the X-Y-Z table 47g may be of the form hereinbefore described with reference to FIGS. 2, 3 and 13 and 15.

The image generating and display components of the embodiment of FIG. 16 may be similar to the corresponding components of the previously described embodiments. X-Y-Z table 47g enables continuous movement or successive repositioning of the detector array 39g to obtain plural images of the examined object from different viewing angles thereby enabling faster identification of defects and faster identification of the best detector location for studying a particular defect.

A particularly useful motion path for the detector or detector array 39g is a circular arc movement about an axis of revolution that extends through the examined object 41g in parallel relationship with the X-axis defined by X-axis slide 189. The angular positioner 177g may then be used to turn the detector array 39g in the course of such motion to maintain the detectors 23g directed towards the axis of revolution. This causes the distance between each detector 23g and a particular point within the object 41g to remain constant as the viewing angle changes. This facilitates interpretation of the images as magnification changes do not occur between successive images.

The multi-angle viewing capability makes the embodiment of FIG. 16 particularly useful for inspecting multi-layered objects 41g such as multi-layered circuit boards or surface mount circuit boards having components on both sides of the board. This capability also facilitates locating of voids in the solder which is present at through holes in circuit boards.

An installation of the type depicted in FIG. 16 may be used to examine objects 41g that are larger than the raster pattern of x-ray source 22g by providing plural x-ray sources arranged in the manner previously described with reference to FIG. 10 and by translating the objects past the sources with a conveyor belt as described with reference to FIG. 12 or with other types of conveyer.

While the invention has been described with reference to certain particular embodiments for purpose of example, many modifications and variations are possible and it is not intended to limit the invention except as defined in the following claims.

I claim:

1. In a non-tomographic x-ray scanning system for examining internal characteristics of an object which system includes x-ray source means for scanning a charged particle beam in a raster pattern on a target plate to produce x-rays successively at different areas of said plate, at least one x-ray detector for disposition at the opposite side of said object from said x-ray source, said x-ray detector having an x-ray sensitive area and means for producing an electrical output signal that is inactive of x-rays impinging on said sensitive area, said sensitive area being sufficiently small in relation to said raster pattern to cause said output signal to vary in accordance with variations of radiation transmissivity at different regions of said object as said charged particle beam is swept in said raster pattern, the improvement comprising:

traveling means for effecting lateral travel of at least one of said x-ray source and said x-ray detector relative to the other thereof in at least one direction during examination of said object which means enables obtaining of a series of different views of said object during said examination thereof by movement of said one of said x-ray detector and said source, and means for generating a sequence of different x-ray views of said object at successive stages of said lateral travel by correlating variations of said output signals with the position of said charged particle beam in said raster pattern at the time that the variations occur.

2. The apparatus of claim 1 wherein said means for generating a sequence of different x-ray views includes at least one cathode ray tube monitor having a display screen which is impacted by an electron beam that is swept in a raster pattern, means for modulating said electron beam in accordance with said output signal of said detector, and means for synchronizing said raster patterns of said x-ray source means and said monitor.

3. The apparatus of claim 2 wherein said apparatus includes a plurality of said x-ray detectors disposed in spaced apart relationship and forming a detector array, said detectors being spaced apart sufficiently to enable imaging of different regions of said object by utilization of different ones of said detectors, and means for generating different sequences of said x-ray views from the output signals of different ones of said detectors during said lateral travel.

4. The apparatus of claim 3 wherein said means for generating different sequences of said x-ray views includes a plurality of said monitors adapted for displaying images of different regions of said object, each of said monitors being coupled to a different one of said detectors.

5. The apparatus of claim 3 further including switch means for selectively coupling said monitor to different ones of said detectors as said lateral travel of one of said x-ray source means and said array of detectors progresses.

6. The apparatus of claim 3 wherein said means for generating different sequences of said x-ray views includes a signal storage, means for transmitting detector output signals and raster pattern signals to said signal storage for storage therein, and means for selectively generating said different x-ray views from the stored signals.

7. The apparatus of claim 3 further including means for generating a first image at said display screen from the output signal of a first of said detectors and for generating a second image at said display screen from another of said detectors, and means for limiting visibility of said first image to one eye of an observer and for limiting visibility of said second image to the other eye of the observer whereby said observer perceives a three dimensional image of said object.

8. The apparatus of claim 1 wherein said traveling means enables travel of said one of said x-ray source means and said detector independently of movement of the other thereof in at least a second direction that is orthogonal to said one direction of said lateral travel.

9. The apparatus of claim 1 wherein said traveling means enables linear travel of said one of said x-ray source means and said detector independently of movement of the other thereof in each of three mutually orthogonal directions.

10. The apparatus of claim 9 wherein said traveling means enables selective tilting of said one of said x-ray source means and said detector about a first axis of rotation that is parallel to said one direction.

11. The apparatus of claim 10 wherein said traveling means further enables selective swiveling of said one of said x-ray source means and said detector about a second axis of rotation that is orthogonal to said first axis of rotation.

12. The apparatus of claim 1 wherein said traveling means includes a maneuverable vehicle having said x-ray source means carried thereon.

13. The apparatus of claim 12 wherein said vehicle includes means for selectively raising and lowering said x-ray source means.

14. The apparatus of claim 13 wherein said vehicle further includes means for selectively extending said x-ray source means outward from said vehicle and for selectively retracting said x-ray source means back towards said vehicle and means for selectively turning said x-ray source means about a horizontal axis of rotation and about a vertical axis of rotation.

15. The apparatus of claim 1 wherein said apparatus includes a plurality of said x-ray detectors which are disposed in at least one row thereof and wherein said traveling means travels said x-ray source means along said row of detectors to produce said series of different views of said object.

16. The apparatus of claim 1 wherein said traveling means jointly travels said detector and said object relative to said x-ray source means.

17. The apparatus of claim 1 wherein said traveling means also provides for rotary motion of said detector relative to said object about an axis of rotation that extends from the vicinity of said detector towards said object and said x-ray source means, said detector being at a location that is offset from said axis.

18. The apparatus of claim 17 wherein said apparatus includes a plurality of x-ray detectors, said plurality of detectors being disposed in an array which extends orthogonally relative to said axis of rotation.

19. The apparatus of claim 17 wherein said traveling means further provides for translation of said detector in each of two directions which are orthogonal to each other and orthogonal to said axis of rotation.

20. In an x-ray scanning system for examining internal characteristics of an object which system includes x-ray source means for scanning a charged particle beam in a raster pattern on a target plate to produce x-rays successively at different areas of said plate, at least one x-ray detector for disposition at the opposite side of said object from said x-ray source, said x-ray detector having an x-ray sensitive area and means for producing an electrical output signal that is inactive of x-rays impinging on said sensitive area, said sensitive area being sufficiently small in relation to said raster pattern to cause said output signal to vary in accordance with variations of radiation transmissivity at different regions of said object as said charged particle beam is swept in said raster pattern, the improvement comprising:
   traveling means for effecting lateral travel of at least one of said x-ray source and said x-ray detector relative to the other thereof in at least one direction during examination of said object, and
   means for generating a sequence of different x-ray views of said object at successive stages of said lateral travel by correlating variations of said output signals with the position of said charged particle beam in said raster pattern at the time that the variations occur, wherein said means for generating a sequence of different x-ray views includes at least one cathode ray tube monitor having a display screen which is impacted by an electron beam that is swept in a raster pattern, means for modulating said electron beam in accordance with said output signal of said detector, and means for synchronizing said raster patterns of said x-ray source means and said monitor,
   wherein said apparatus includes a plurality of said x-ray detectors disposed in spaced apart relationship and forming a detector array and means for generating different sequences of said x-ray views from the output signals of different ones of said detectors suring said lateral travel,
   further including means for generating a first image at said display screen from the output signal of a first of said detectors and for generating a second image at said display screen from another of said detectors, and means for limiting visibility of said first image to one eye of an observer and for limiting visibility of said second image to the other eye of the observer whereby said observer perceives a three dimensional image of said object, and
   wherein said detectors are arranged in spaced apart pairs which provides the output signals for generating said first and second images, the numbers of each pair being spaced apart a distance that is smaller than the spacing of successive pairs from each other.

21. In an x-ray scanning system for examining internal characteristics of an object which system includes x-ray source means for scanning a charged particle beam in a raster pattern on a target plate to produce x-rays successively at different areas of said plate, at least one x-ray detector for disposition at the opposite side of said object from said x-ray source, said x-ray detector having an x-ray sensitive area and means for producing an electrical output signal that is indicative of x-rays impinging on said sensitive area, said sensitive area being sufficiently small in relation to said raster pattern to cause said output signal to vary in accordance with variations of radiation transmissivity at different regions of said object as said charged particle beam is swept in said raster pattern, the improvement comprising:

traveling means for effecting lateral travel of at least one of said x-ray source and said x-ray detector relative to the other thereof in at least one direction during examination of said object, and means for generating a sequence of different x-ray views of said object at successive stages of said lateral travel by correlating variations of said output signals with the position of said charged particle beam in said raster pattern at the time that the variations occur, wherein said x-ray source means includes a plurality of vacuum tubes each having a face defined by a separate one of said target plates, said faces of said vacuum tubes being positioned to jointly provide a continuous x-ray origin area which is of greater extent in a direction normal to the direction of said lateral travel than the raster patterns at a single one of said target plates.

22. The apparatus of claim 21 wherein said target plates of said plurality of vacuum tubes are co-planar and wherein the raster patterns at said target plates are rectangular and wherein an edge of the raster pattern at each target plate is in alignment with an edge of the raster pattern at an adjacent one of said target plates.

23. In an x-ray scanning system for examining internal characteristics of an object which system includes x-ray source means for scanning a charged particle beam in a raster pattern on a target plate to produce x-rays successively at different areas of said plate, at least one x-ray detector for disposition at the opposite side of said object from said x-ray source, said x-ray detector having an x-ray sensitive area and means for producing an electrical output signal that is indicative of x-rays impinging on said sensitive area, said sensitive area being sufficiently small in relation to said raster pattern to cause said output signal to vary in accordance with variations of radiation transmissivity at different regions of said object as said charged particle beam is swept in said raster pattern, the improvement comprising:

traveling means for effecting lateral travel of at least one of said x-ray source and said x-ray detector relative to the other thereof in at least one direction during examination of said object, and means for generating a sequence of different x-ray views of said object at successive stages of said lateral travel by correlating variations of said output signals with the position of said charged particle beam in said raster pattern at the time that the variations occur, wherein said traveling means enables translation of said detector in each of three mutually orthogonal directions and also enables turning of said detector about an axis of rotation that extends in parallel relationship with said target plate of said x-ray source means.

24. The apparatus of claim 23 further including a cabinet having walls formed at least in part of x-ray absorbent shielding material, said detector and said x-ray source means being disposed in said cabinet, further including means for supporting said object within said cabinet at a location that is between said detector and said x-ray source means.

25. In a method for examining internal characteristics of an object which system includes the steps of generating x-rays at an x-ray origin point, moving said origin point in a raster pattern to define a raster area, locating said object in the path of x-rays that are emitted from said raster area, detecting said x-rays at least at one detection point and producing an electrical output signal in response to the detected x-rays that is indicative of variations of x-ray transmissivity within the scanned region of said object, the improvement comprising:

traveling at least one of said raster area and said detection point laterally relative to the other thereof during the examination of said object to generate output signals for producing a series of different views of said object, and using the output signals that originate at successive locations along the path of travel of said one of said raster area and said detection point to generate a sequence of different non-topographic x-ray views of said object.

26. The method of claim 25 wherein said object has at least one curved or angled surface including the further steps of successively detecting said x-rays at a plurality of spaced apart detection points during said lateral travel, said detection points being maintained in fixed spacial relationship to each other during said travel, and tilting and swiveling said one of said raster area and said plurality of detection points during said lateral travel about orthogonal axes of rotation and translating said one of said raster area and said plurality of detection points in three orthogonal directions in order to maintain said raster area in facing relationship with at least one of said detection points.

27. The method of claim 25 wherein said object is an aircraft having a fuselage and wherein said x-rays are detected at a plurality of detection points situated within said fuselage at spaced apart intervals therealong, including the further steps of situating said raster area outside of said fuselage and traveling said raster area along said fuselage and upward and downward relative to said fuselage and reorienting said raster area to direct said x-rays to different ones of said detection points and different locations along said fuselage.

28. The method of claim 27 including the further steps of generating said x-rays on board a powered mobile vehicle and utilizing said vehicle to travel said raster area along said fuselage.

29. The method of claim 25 including the further step of jointly turning said x-ray detection point about an axis of rotation that extends toward said object and which is different from said detection point whereby said x-ray views include views of the same regions of said object taken at different angles.

30. In a method for examining internal characteristics of an object which includes the steps of generating x-rays at an x-ray origin point, moving said origin point in a raster pattern to define a raster area, locating said object in the path of x-rays that are emitted from said raster area, detecting said x-rays at least at one detection point and producing an electrical output signal in response to the detected x-rays that is indicative of variations of x-ray transmissivity within the scanned region of said object, the improvement comprising:

traveling at least one of said raster area and said detection point laterally relative to the other during the examination of said object, and using the output signals that originate at successive locations along the path of travel of said one of said raster area and said detection point to generate a sequence of different x-ray views of said object, wherein said x-ray detection point is traveled along a circular path about an axis of rotation that is substantially parallel to said raster area and which intersects said object.

31. The method of claim 30 wherein said x-rays are detected at a plurality of detection points which are spaced apart in a coplanar array that is parallel to said axis of rotation, including the further step of turning said array of detection points about another orthogonal axis of rotation as said detection point is traveled along said circular path.

* * * * *